US009931501B2

(12) United States Patent
Smyth

(10) Patent No.: US 9,931,501 B2
(45) Date of Patent: Apr. 3, 2018

(54) IMPLANTABLE AUDITORY PROSTHESIS HAVING ISOLATED COMPONENTS

(71) Applicant: Daniel Smyth, Macquarie University (AU)

(72) Inventor: Daniel Smyth, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 0 days.

(21) Appl. No.: 14/310,159

(22) Filed: Jun. 20, 2014

(65) Prior Publication Data
US 2015/0367126 A1 Dec. 24, 2015

(51) Int. Cl.
*A61N 1/08* (2006.01)
*A61N 1/05* (2006.01)
*A61N 1/375* (2006.01)

(52) U.S. Cl.
CPC ............. *A61N 1/0541* (2013.01); *A61N 1/08* (2013.01); *A61N 1/375* (2013.01)

(58) Field of Classification Search
CPC ...... A61N 1/08; A61N 1/36032; A61N 1/375; A61N 1/0541
USPC ................................ 607/57, 61, 137; 623/10
See application file for complete search history.

(56) References Cited

U.S. PATENT DOCUMENTS

2012/0022647 A1  1/2012  Leigh et al.
2014/0343626 A1*  11/2014  Thenuwara et al. ............ 607/57

* cited by examiner

*Primary Examiner* — Carl H Layno
*Assistant Examiner* — Jon Eric C Morales
(74) *Attorney, Agent, or Firm* — Merchant & Gould P.C.

(57) ABSTRACT

A magnet is completely encased within a body of a biocompatible implant. The body of the biocompatible implant is formed so as to allow for removal of the magnet after implantation in a recipient. The body includes a portion that is at least partially separable from the remainder of the body, either by application of a removing agent or a tool. The magnet can be removed and replaced. Thereafter, the body can be sealed or the magnet can be left exposed.

16 Claims, 13 Drawing Sheets

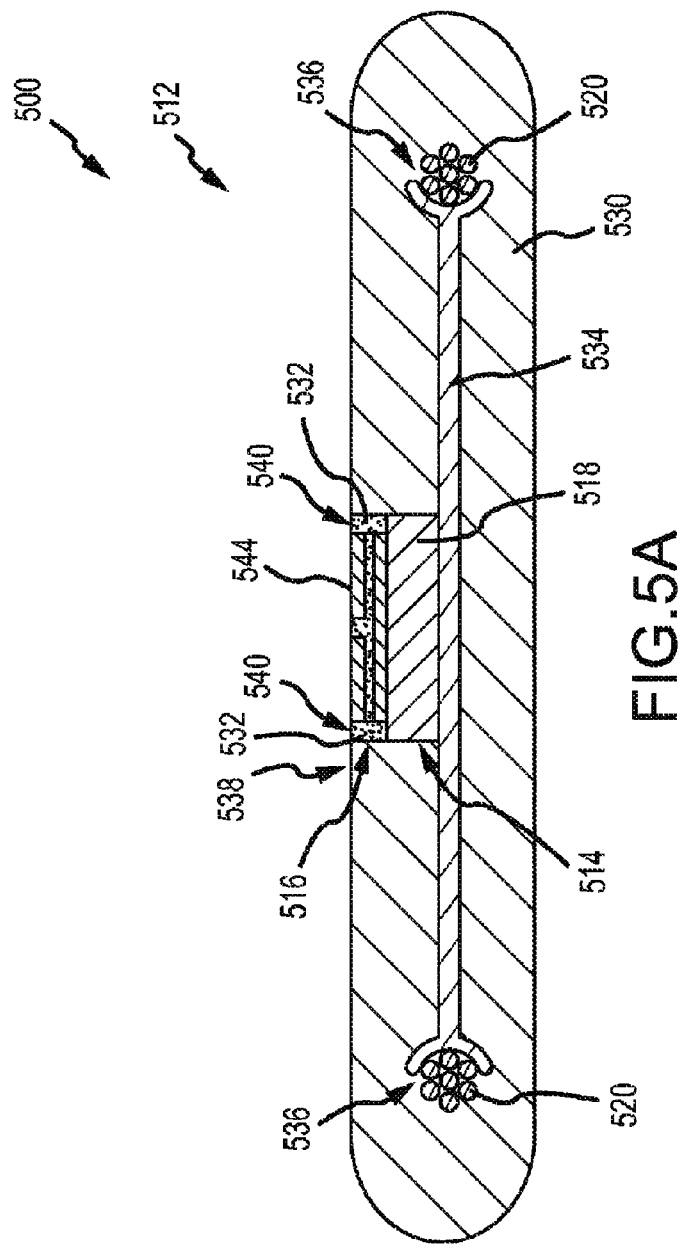
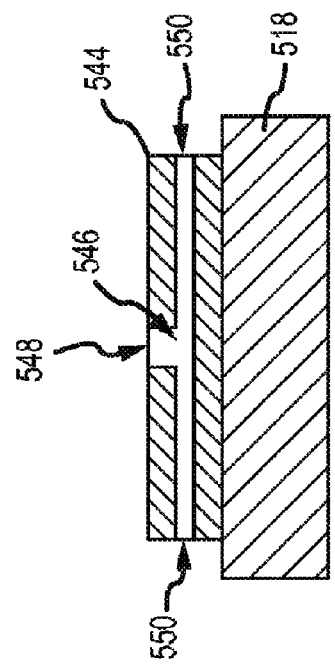
FIG.5A
FIG.5B

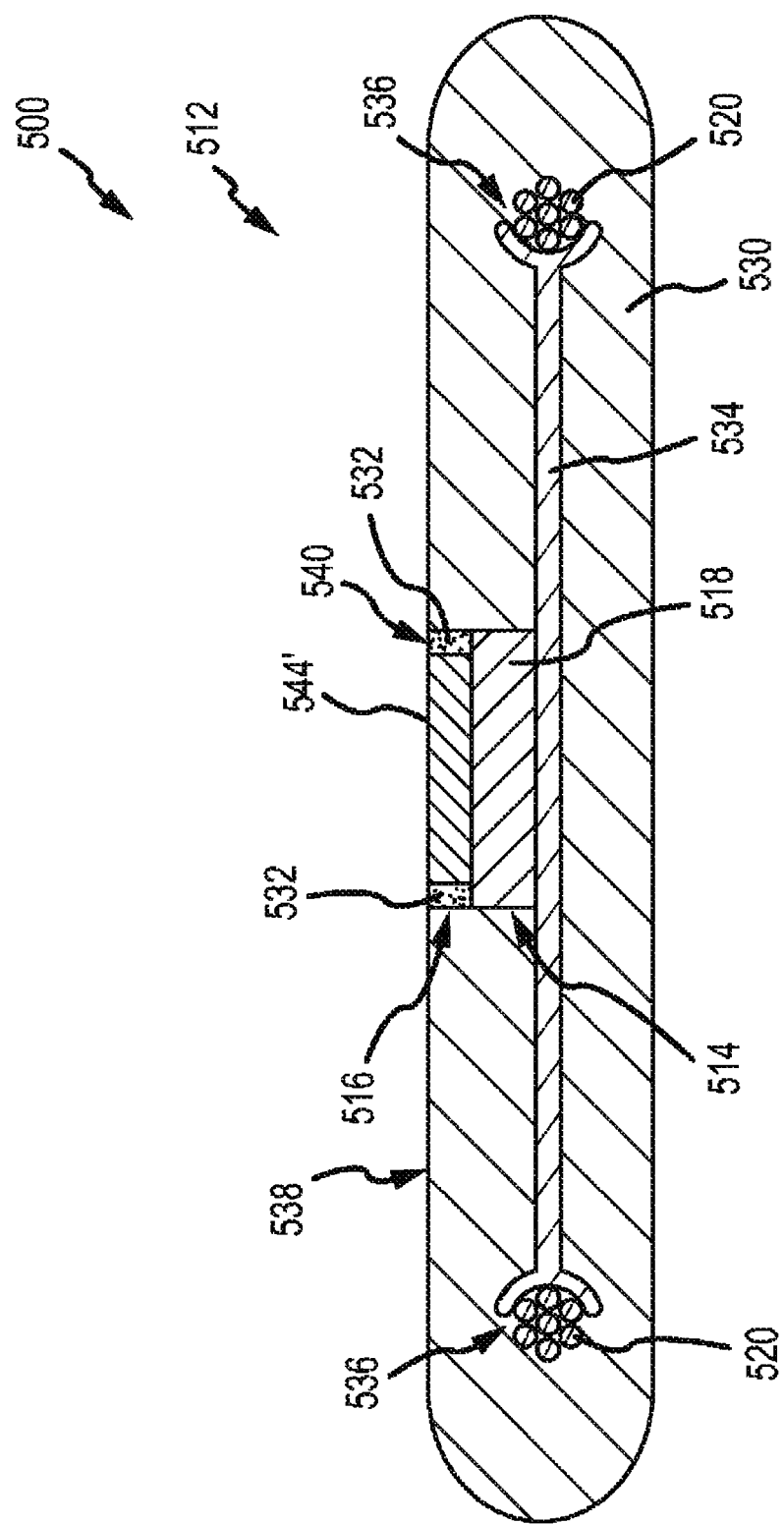

IMPLANTABLE AUDITORY PROSTHESIS HAVING ISOLATED COMPONENTS

BACKGROUND

An auditory prosthesis can be placed behind the ear to deliver a stimulus in the form of an electrical signal to the cochlea of a recipient. These types of auditory prosthesis are generally referred to as cochlear implants. The auditory prosthesis receives sound via a microphone located on a behind-the-ear (BTE) device. The sound is processed and converted to electrical signals, which are sent to an external portion of the auditory prosthesis. The external portion is secured to the head with a magnet that interacts with an implanted magnet in an implanted portion in the recipient's head. Electrical signals are delivered to a coil of the implanted portion from a coil of the external portion. Typically, the implanted magnet is at least partially exposed to the implantation site. This is desirable because removal of the magnet is required if the recipient undergoes, e.g., an MRI procedure. It has been discovered that biofilms (clusters or communities of bacteria that can form on an implanted device and lead to infection) can form on the magnet, generally proximate the interface with the implant itself.

SUMMARY

The technologies disclosed herein generally relate to completely sealing a magnet within the body of a cochlear implant, so as to reduce the likelihood of adhesion of biofilms and bacteria. In some embodiments, a portion of the body can be separated from the remainder of the body, so as to allow removal of the magnet. The magnet can be later replaced, and the body resealed, if desired.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Similar numbers represents the same element or same type of element in all drawings.

FIG. 5A is a cross-sectional view of another embodiment of an implantable portion of a cochlear implant.

FIG. 5B is an enlarged cross-sectional view of a magnet utilized in the implantable portion of FIG. 5A.

FIG. 5C is a cross-sectional view of another embodiment of an implantable portion of a cochlear implant.

DETAILED DESCRIPTION

The technologies described herein can typically be utilized with auditory prostheses such as cochlear implants. Such devices utilize one or more magnets disposed in an external portion of the cochlear implant. The magnetic field of this external magnet interacts with a magnetic field of a magnet disposed in an implanted portion of the cochlear implant. The technologies disclosed herein have further application in any type of medical device implanted in a recipient. For example, other types of auditory prostheses, such as transcutaneous bone conduction devices and direct acoustic stimulators utilize a similar configuration where a magnet is implanted below the skin of a recipient. Accordingly, the technologies described herein can be similarly leveraged in such devices. The technologies described herein can also be utilized in medical devices having certain components that can require removal (and replacement) at some point after implantation. Such devices include, for example, totally implantable cochlear implants, which can require removal and replacement of an implanted battery. Other components, such as chips, coils, and so on, can also be removed and replaced. For clarity, however, the technologies will be described in the context of implanted, replaceable magnets for cochlear implants.

Figure 1:
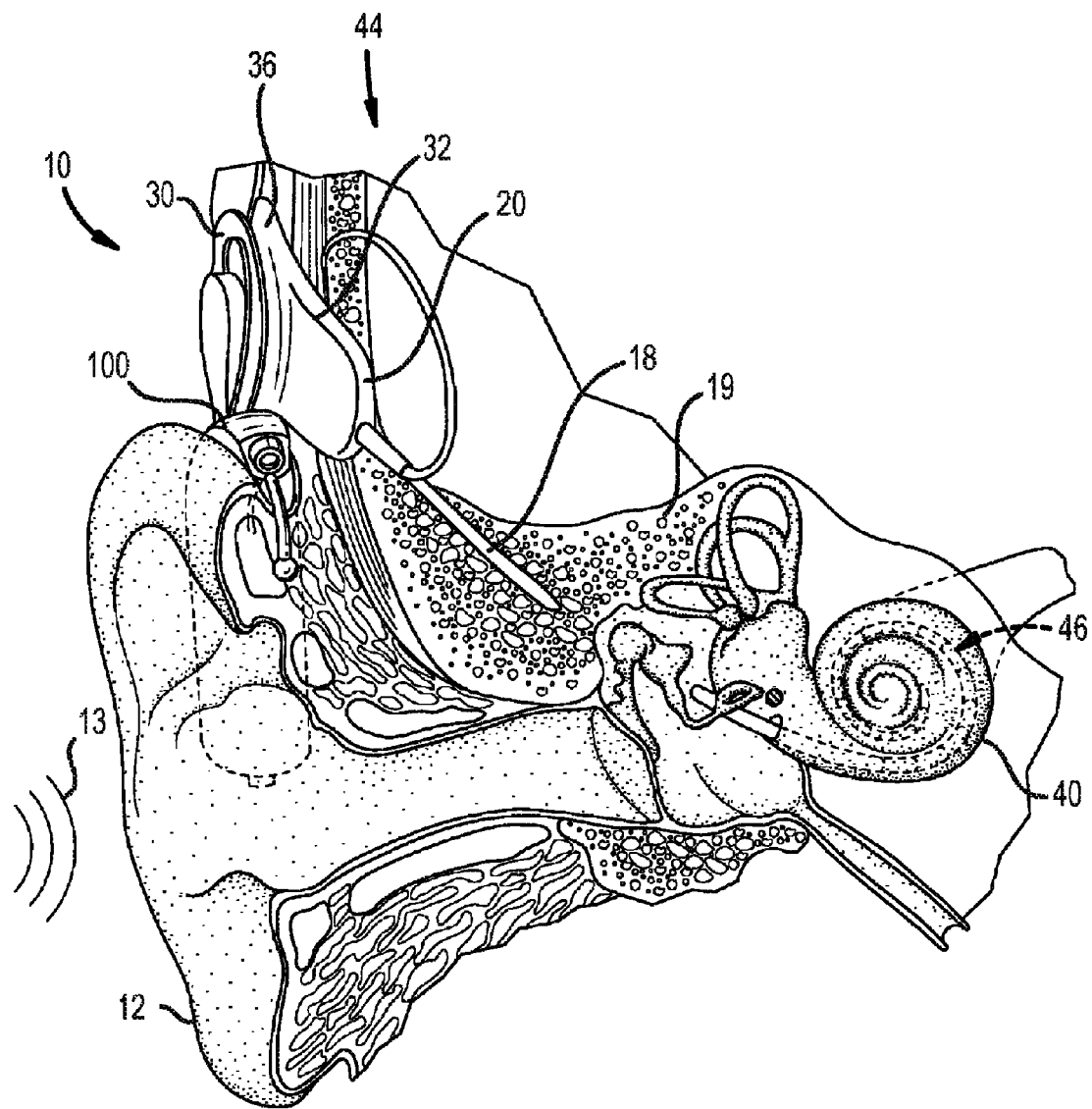
FIG. 1 is a partial view of a cochlear implant auditory prosthesis worn on a recipient.

Referring to FIG. 1, cochlear implant system 10 includes an implantable component 44 typically having an internal receiver/transceiver unit 32, a stimulator unit 20, and an elongate lead 18. The internal receiver/transceiver unit 32 permits the cochlear implant system 10 to receive and/or transmit signals to an external device 100 and includes an internal coil 36, and preferably, a magnet (not shown) fixed relative to the internal coil 36. These signals generally correspond to external sound 13. Internal receiver unit 32 and stimulator unit 20 are hermetically sealed within a biocompatible housing, sometimes collectively referred to as a stimulator/receiver unit. The magnets facilitate the operational alignment of the external and internal coils, enabling internal coil 36 to receive power and stimulation data from external coil 30. The external coil 30 is contained within an external portion. Elongate lead 18 has a proximal end connected to stimulator unit 20, and a distal end implanted in cochlea 40. Elongate lead 18 extends from stimulator unit 20 to cochlea 40 through mastoid bone 19.

In certain examples, external coil 30 transmits electrical signals (e.g., power and stimulation data) to internal coil 36 via a radio frequency (RF) link, as noted above. Internal coil 36 is can be, by way of example, a coil including one or more turns of single-strand or multi-strand wire. The wire can be made from platinum, gold, or other similar materials or combinations. Various types of energy transfer, such as infrared (IR), electromagnetic, capacitive and inductive transfer, can be used to transfer the energy (e.g., power) and/or data, from external device to cochlear implant.

There are a variety of types of intra-cochlear stimulating assemblies including short, straight and peri-modiolar. A peri-modiolar stimulating assembly 46 is configured to adopt a curved configuration during and or after implantation into the recipient's cochlea 40. To achieve this, in certain arrangements, stimulating assembly 46 is pre-curved to the same general curvature of a cochlea 40. Such examples of stimulating assembly 46, are typically held straight by, for example, a stiffening stylet (not shown) or sheath which is removed during implantation, or alternatively varying material combinations or the use of shape memory materials, so that the stimulating assembly can adopt its curved configuration when in the cochlea 40. Other methods of implantation, as well as other stimulating assemblies, can be used.

Figure 2:
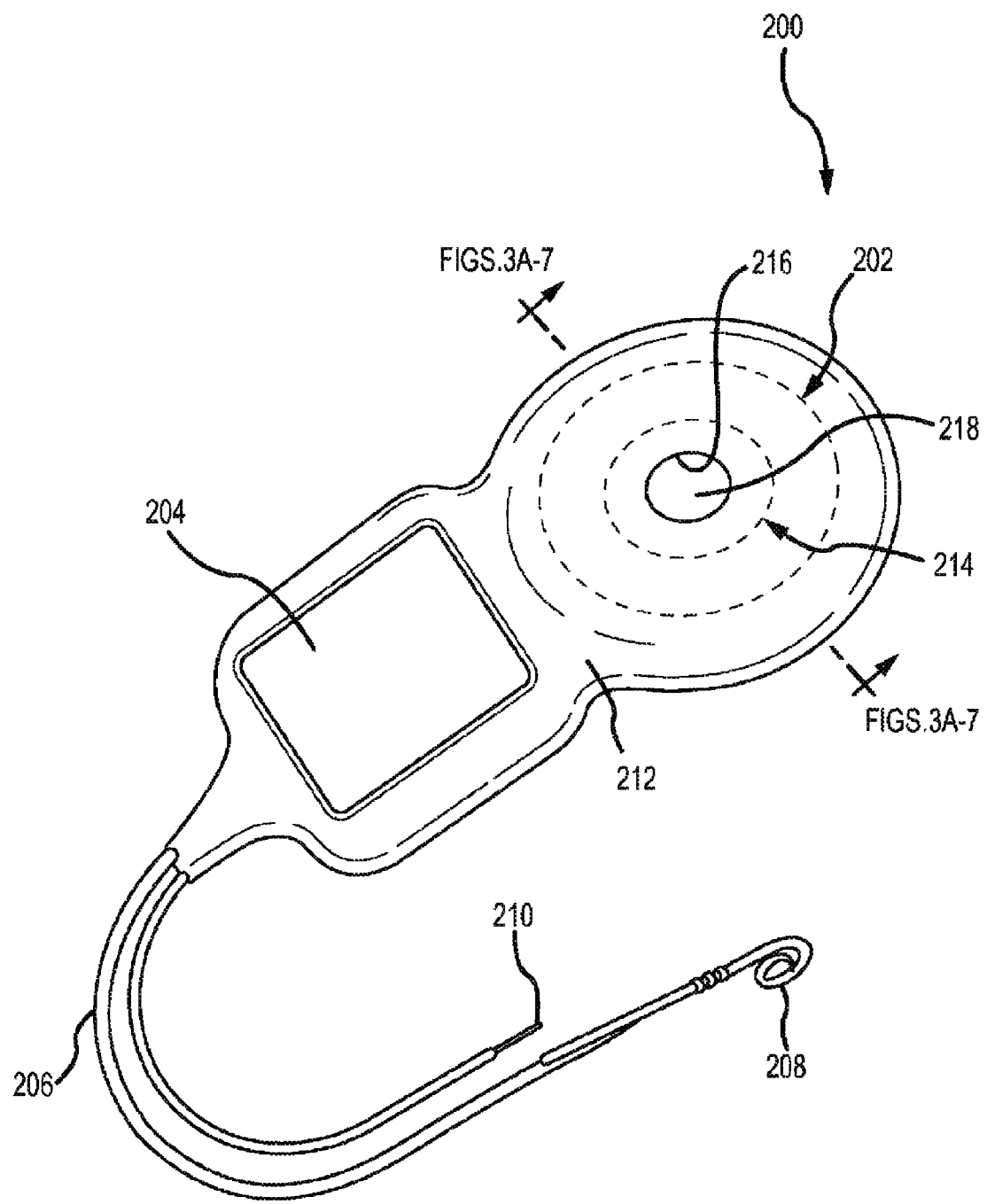
FIG. 2 is a perspective view of an implantable portion of a cochlear implant.

FIG. 2 is a perspective view of one example of an implantable portion 200 of a cochlear implant. The implantable portion 200 functions as a receiver/stimulator and includes a coil 202 and a stimulator unit 204, with an electrode lead 206 terminating in an electrode assembly 208 and a reference electrode 210 extending from the stimulator unit 204. The implantable portion 200 is formed at least partially of a biocompatible body 212. The biocompatible body 212 defines a void or pocket 214 having an aperture or throat 216 via which a magnet 218 is inserted into the pocket 214. The coil 202 that that receives and sends electrical signals to an associated coil in the external portion of the cochlear implant.

The technologies described herein temporarily isolate the magnet and its pocket from exposure to fluids, tissues, and so on, present in the implantation site within the recipient so as to ameliorate the risks of biofilm formation. For recipients that require temporary removal of the magnet (for example, during a MRI procedure), that recipient can chose to reseal the magnet pocket after the magnet is replaced. Resealing is described below.

The throat 216 can be sealed in different ways to isolate the magnet from exposure with an implantation site within a recipient. Several examples of contemplated sealing systems are disclosed herein. By isolating the magnet 218 from the implantation site, occurrence of biofilms on the magnet 218 and exposed portions of the pocket 214 and the throat 216 is reduced or eliminated because a site of potential bacterial adhesion is eliminated. In general, the sealing systems described herein utilize biocompatible materials to isolate the magnet 218 from exposure to the implantation site. The embodiments of sealing systems described herein completely, but removably, encase the magnet 218 within the biocompatible body 212. The body 212 can be manufactured of multiple materials so as to removably encase the magnet 218 therein. A majority, first portion, of the body 212 is manufactured of a first body material such as silicone, polyurethane, or other suitable biocompatible materials. A minority, second portion, of the body is manufactured of a second body material such as cyanoacrylate, polypropylene, polyethylene, polyvinyl acetate, poly(methyl methacrylate) (PMMA), or other material. In certain embodiments, silicone having a lower crosslink density than the first body material can be utilized for the second body material. In one embodiment, the first and second body materials can be the same materials. This second body material is disposed proximate the magnet 218 and can be subsequently separated from the first body material to allow for removal of the magnet 218. The second body material can bond to the first body material so as to seal the throat 216. Thus, the technologies disclosed herein utilize one or more body materials to completely seal the throat 216 of the implantable body 212, to isolate the magnet 218 from the implantation site.

Figure 3A:
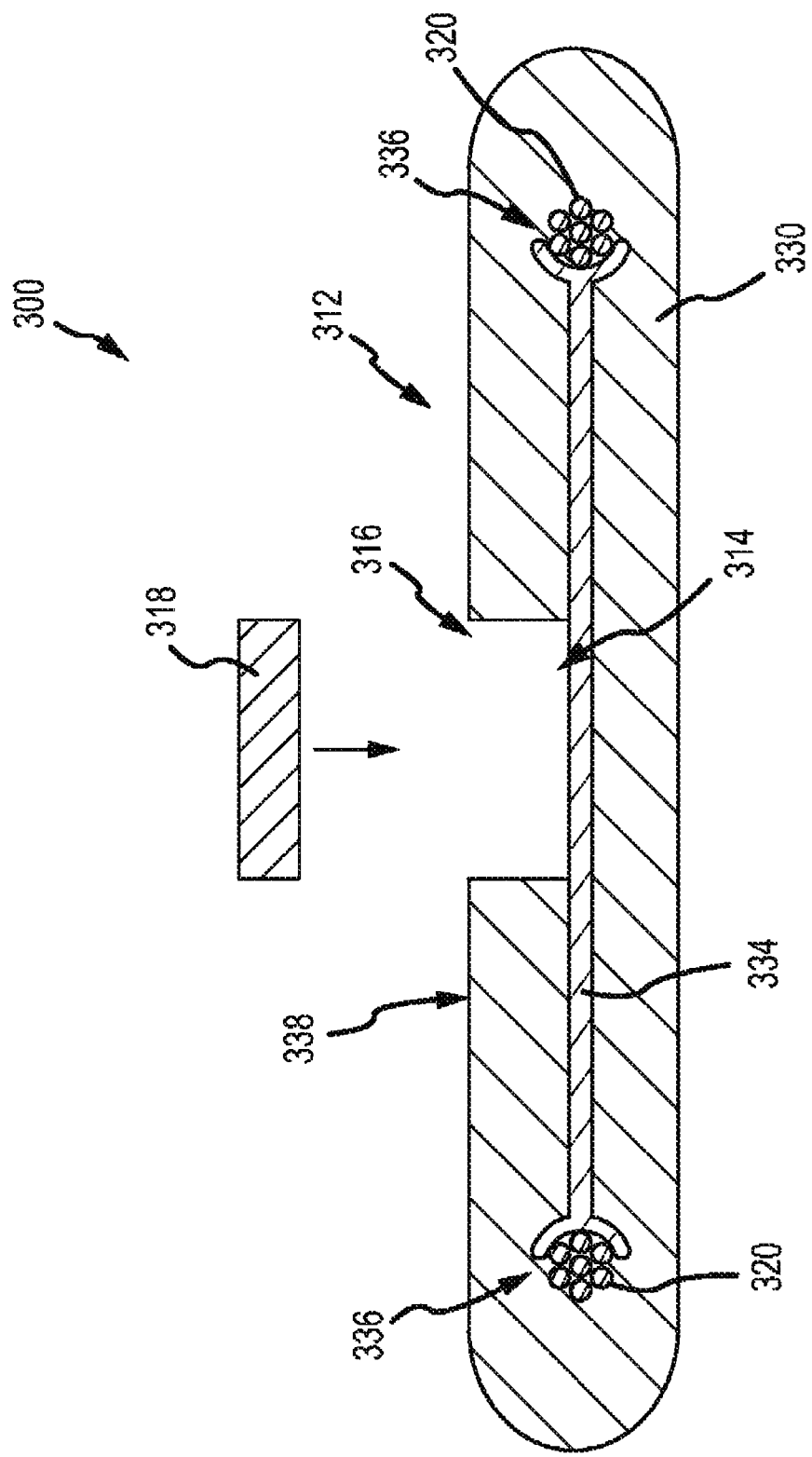
FIGS. 3A and 3B are cross-sectional views of an embodiment of an implantable portion of a cochlear implant.
Figure 3B:
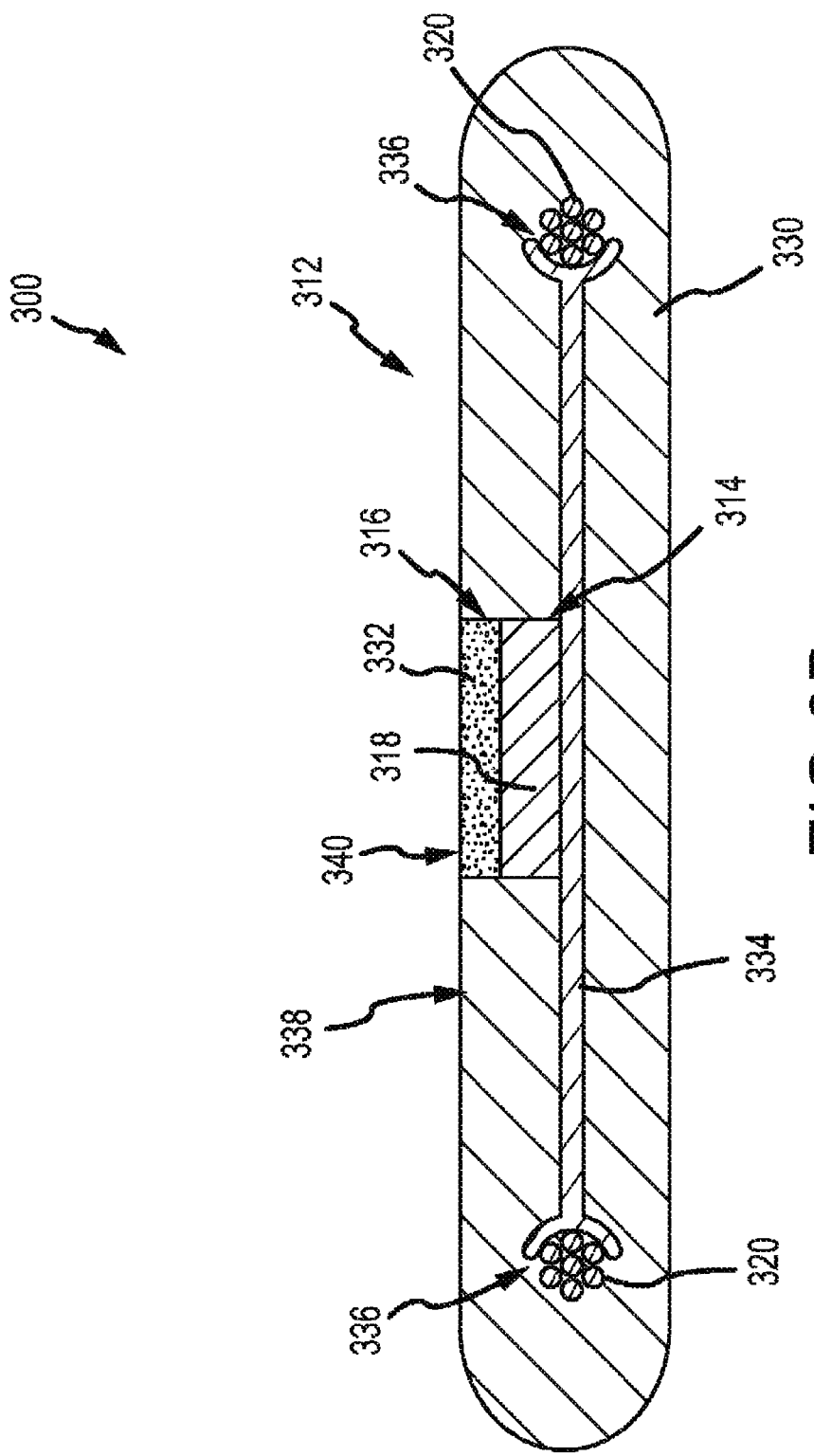

FIGS. 3A and 3B are cross-sectional views of an embodiment of an implantable portion 300 of a cochlear implant and are described together. A biocompatible body 312 is formed from a first body material 330 and a second body material 332. The first body material 330 surrounds a base 334, which can be disk-shaped or have another shape as required or desired for a particular application. The base 334 provides some rigidity to the implantable portion 300, but is not required. In certain embodiments, the base 334 forms a channel or race 336 configured to at least partially receive a coil 320. The coil 320 is formed by a winding of wires and is encased in the first body material 330. The first body material 330 defines a pocket 314 and a throat 316 proximate an exterior surface 338 of the first body material 330. A magnet 318 is received within the pocket 314, via insertion through the throat 316. This insertion is depicted in FIG. 3A. Once the magnet 318 is inserted, the throat 316 can be sealed with the second body material 332, prior to implantation within a recipient. In the depicted embodiment, the pocket 314 is sized so as to tightly fit the magnet 318. Thus, the second body material 332 simply covers the magnet 318 and bonds to the first body material 330 at the throat 316. In other embodiments, the pocket 314 can be oversized, relative to the magnet 318. In such an embodiment, the second body material 332 can completely or partially fill the pocket 314, not just the throat 316.

Regardless, the second body material 332 is applied so as to seal to the throat 316 to isolate the magnet 318 within the biocompatible body 312. Typically, the second body material 332 is applied in a liquid or viscous state. In one embodiment, after application of the second material, the upper surface 340 of the second body material 332 is shaped so as to be substantially level or flush with the exterior surface 338 of the first body material 330. Such shaping helps reduce the number and size of edges, steps, cracks, seams, or other imperfections in the biocompatible body 312, which reduces the number of sites of potential bacterial adhesion. Shaping the upper surface 340 also reduces surface variances that can cause pressure points on the skin once the implantable portion 300 is implanted in an implant site. The second body material 332 can later be at least partially separated from the body 312 so as to allow removal of the magnet 318. In certain embodiments, substantially all of the second body material 332 can be completely removed from the pocket 314 and throat 316. Methods of removing the second body material are described below. Additionally, the second body material 332 can be applied so as not to contact the magnet 318, or the magnet 318 can be coated with, or manufactured from, a material that resists adhesion to the second body material 332, to increase ease of separation and removal.

Figure 4A:
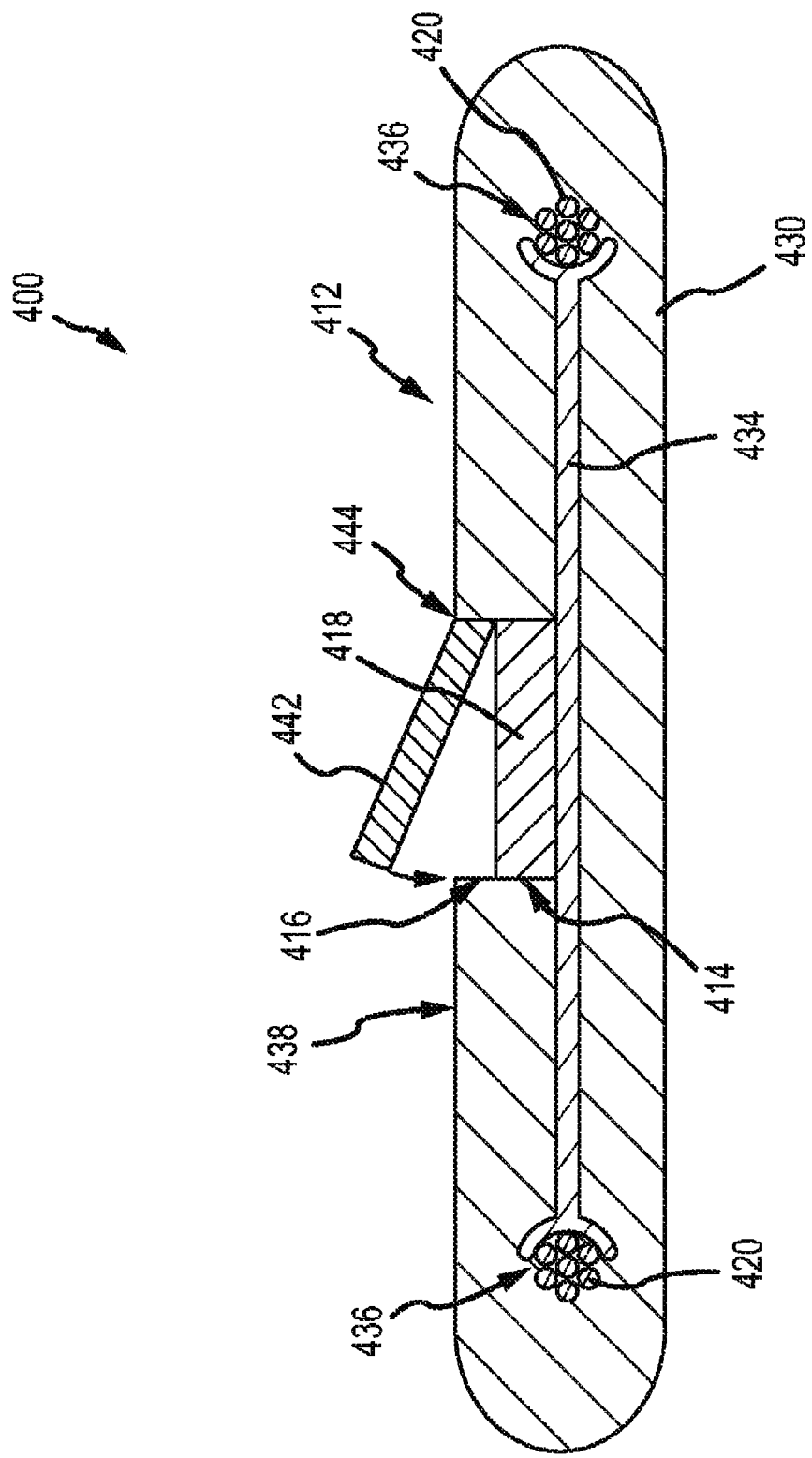
FIGS. 4A and 4B are cross-sectional views of other embodiments of implantable portions of a cochlear implant.
Figure 4B:
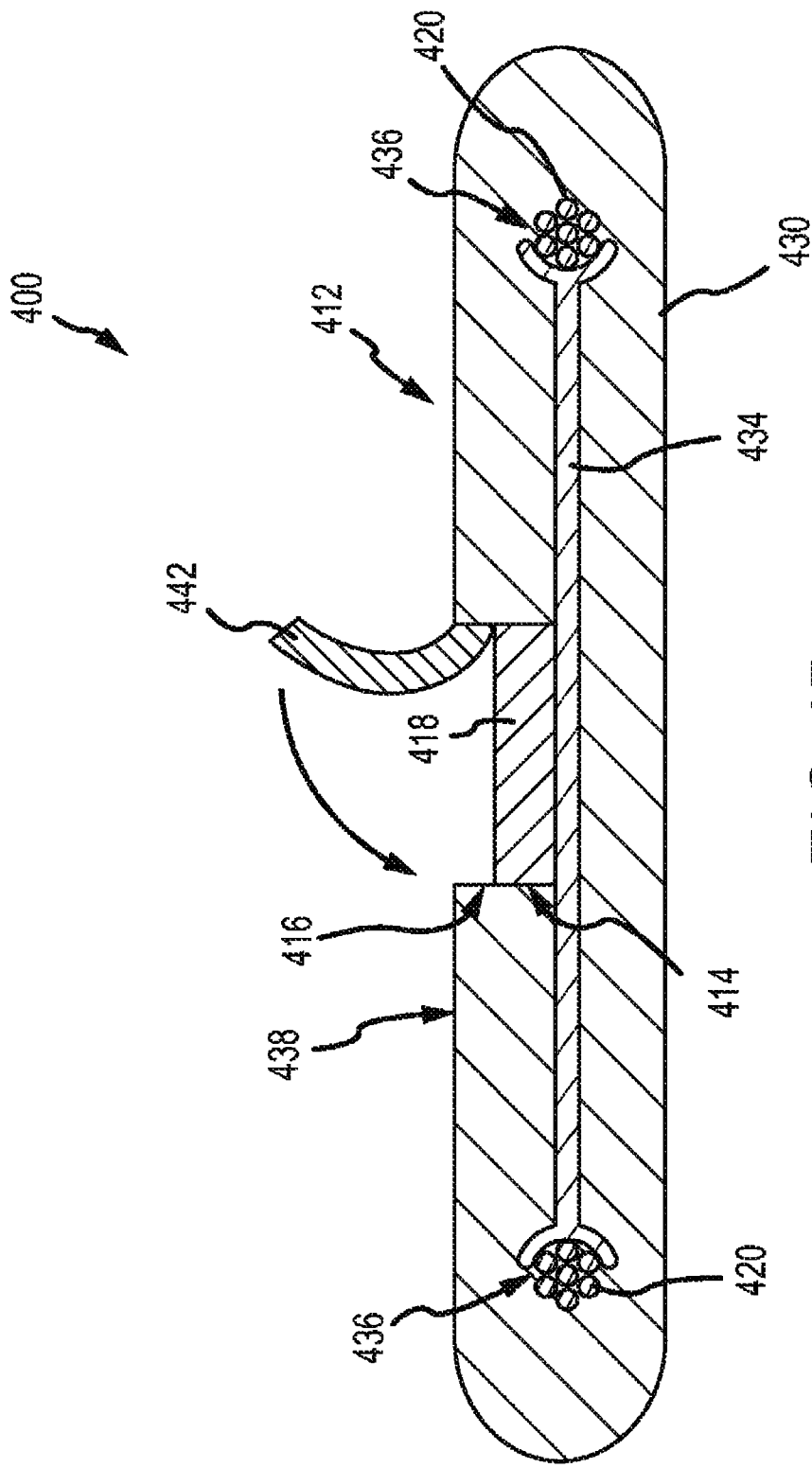
Figure 4C:
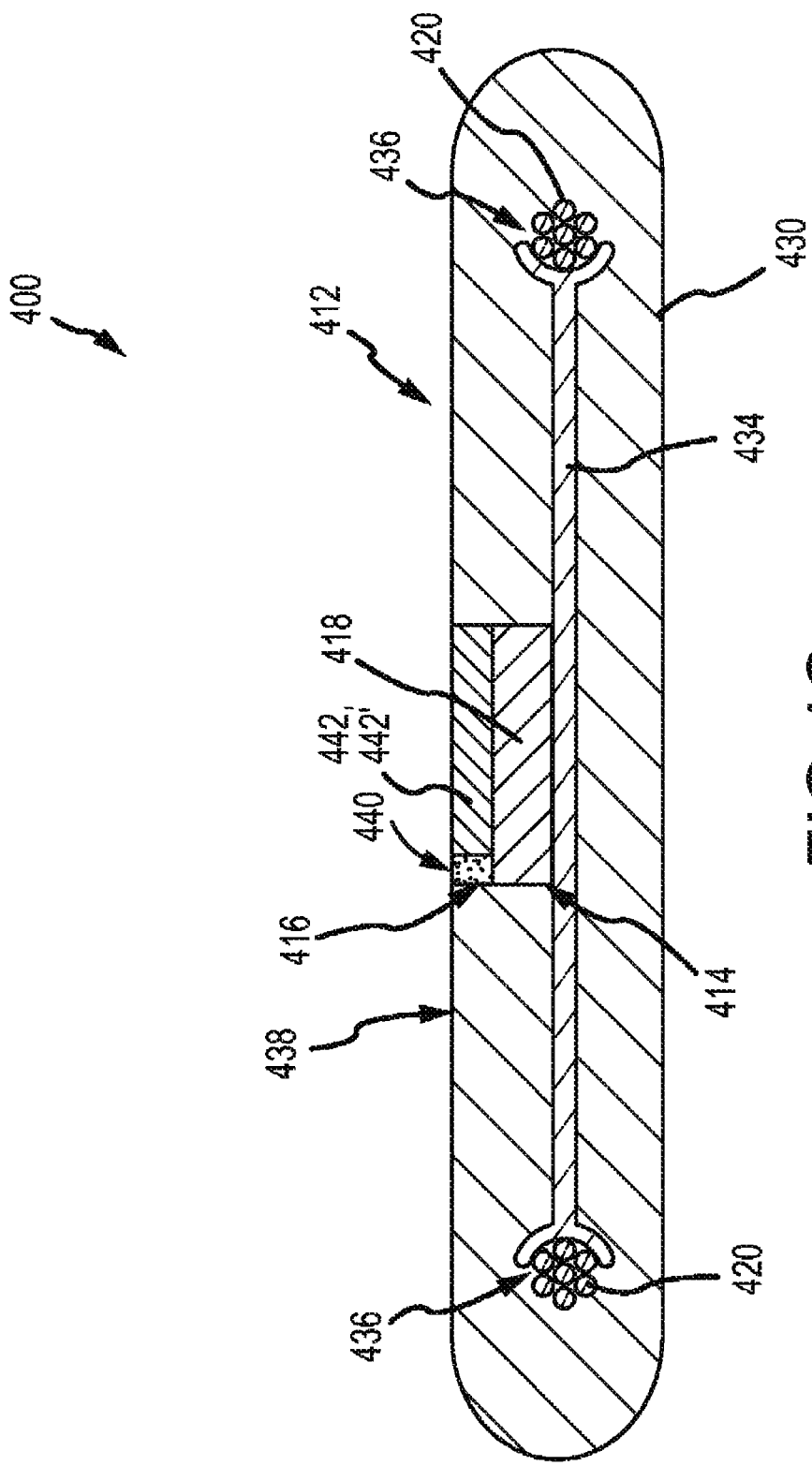
FIG. 4C is a cross-sectional view of the implantable portions of FIGS. 4A and 4B, in a sealed configuration.

FIGS. 4A and 4B are cross-sectional views of others embodiment of an implantable portion 400 of a cochlear implant and are described simultaneously with FIG. 4C, which depicts the embodiments of FIGS. 4A and 4B in a sealed configuration. Certain components of the implantable portion 400 are described above with regard to the embodiment of FIGS. 3A and 3B, and are therefore only described briefly. The implantable portion 400 includes a biocompatible body 412 formed from a first body material 430 and a second body material 432. The first body material 430 surrounds a base 434 that provides some rigidity to the implantable portion 400, but is not required. The base 434 forms a channel or race 436 configured to at least partially receive a coil 420, formed by a winding of wires. The first body material 430 defines a pocket 414 and a throat 416 proximate an exterior surface 438 of the first body material 430. A magnet 418 is received within the pocket 414, via insertion through the throat 416. A rigid flap 442 is disposed proximate the throat 416 and is connected to the first body material 430 at a flexible hinge 444. In another embodiment, depicted in FIG. 4B, the flap 442' is flexible and is connected to the first body material 430 without requiring the flexible hinge 444 of the embodiment of FIG. 4A. The flap 442, 442' can be integral with the first body portion 430 and lifted away from the pocket 414 during insertion or removal of the magnet 418. Application of the second body material 440 seals a gap between the flap 442, 442' and the first body material 430, at the throat 416.

In another embodiment, a biocompatible body can be manufactured as depicted in FIGS. 3A and 3B, e.g., with an open pocket 314 and a seal formed by the second body material 332, as depicted in FIG. 3B. To remove the magnet 318, only a portion of the second body material 332 need be removed, thus forming the flap 442, 442' depicted in FIG. 4A or 4B. The flap 442, 442', in such a case, would be made from the second body material 432 and could be resealed. As described above, an upper surface 440 of the second body material 432 can be shaped so as to be even with the exterior surface 438 of the first body material 430. Such shaping helps reduce the number and size of cracks, seams, or other imperfections in the biocompatible body 412, which reduces the number of sites where biofilms can form. Shaping the upper surface 440 also reduces surface variances that can cause pressure points on the skin once the implantable portion 400 is implanted in an implant site.

FIG. 5A is a cross-sectional view of another embodiment of an implantable portion 500 of a cochlear implant. FIG. 5B is an enlarged cross-sectional view of a magnet 518 utilized in the implantable portion 500. Both FIGS. 5A and 5B are described together. Certain components of the implantable portion 500 are described above with regard to the embodiment of FIGS. 3A and 3B, and are therefore only described briefly. The implantable portion 500 includes a biocompatible body 512 formed from a first body material 530 and a second body material 532. The first body material 530 can surround a base 534 that provides rigidity to the implantable portion 500, but is not required. The base 534 forms a channel or race 536 configured to at least partially receive a coil 520, formed by a winding of wires. The first body material 530 defines a pocket 514 and a throat 516 proximate an exterior surface 538 of the first body material 530. A magnet 518 is received within the pocket 514, via insertion through the throat 516. The magnet 518 has secured thereto a plug 544. In another embodiment, the plug 544 can be discrete from the magnet 518. The plug 544 can be manufactured of the same material as the first body material 530 or a different biocompatible material. The plug 544 defines at least one channel 546 that extends from an inlet 548 on a top of the plug 544 to one or more outlets 550 on an edge of the plug 544. Once the magnet 518 is inserted into the pocket 514, the plug 544 rests substantially within the throat 516. In embodiments, the plug 544 can have an area less than the area of the throat 516, such that it does not touch the throat 516. A second body material 532 can then be injected into the inlet 548 such that it is directed through the channel 546 to the outlets 550. As the second body material 532 exits the outlets 550, it seals the throat 516 and isolates the magnet 518, as described above. Also as described above, an upper surface 540 can be shaped to a smooth finish even with the exterior surface 538. Such shaping helps reduce the number and size of cracks, seams, or other imperfections in the biocompatible body 512, which reduces the number of sites where biofilms can form. Shaping the upper surface 540 also reduces surface variances that can cause pressure points on the skin once the implantable portion 500 is implanted in an implant site.

FIG. 5C is a cross-sectional view of another embodiment of an implantable portion 500 of a cochlear implant. Certain components of the implantable portion 500 are described above with regard to the embodiment of FIG. 5A. Like the embodiment depicted in FIG. 5A, the implantable portion 500 of FIG. 5C utilizes a plug 544', that can be discrete from or secured to the battery 518. Once the plug 544' is placed in the throat 516, the throat 516 can be sealed with the second body material 532. Also as described above, an upper surface 540 can be shaped to a smooth finish even with the exterior surface 538. Such shaping helps reduce the number and size of cracks, seams, or other imperfections in the biocompatible body 512, which reduces the number of sites where biofilms can form. Shaping the upper surface 540 also reduces surface variances that can cause pressure points on the skin once the implantable portion 500 is implanted in an implant site. For any of the embodiments of FIGS. 5A-5C, the magnet 518 can still be removed by separating the second body material 532 from the first body material 530. This would allow for removal of the plug 544, 544' and the magnet. In another embodiment, a plug can be slightly larger than the throat 516. The second body material 532 can be used to secure or adhere this larger edge of the plug around the perimeter of the throat 516.

Figure 6:
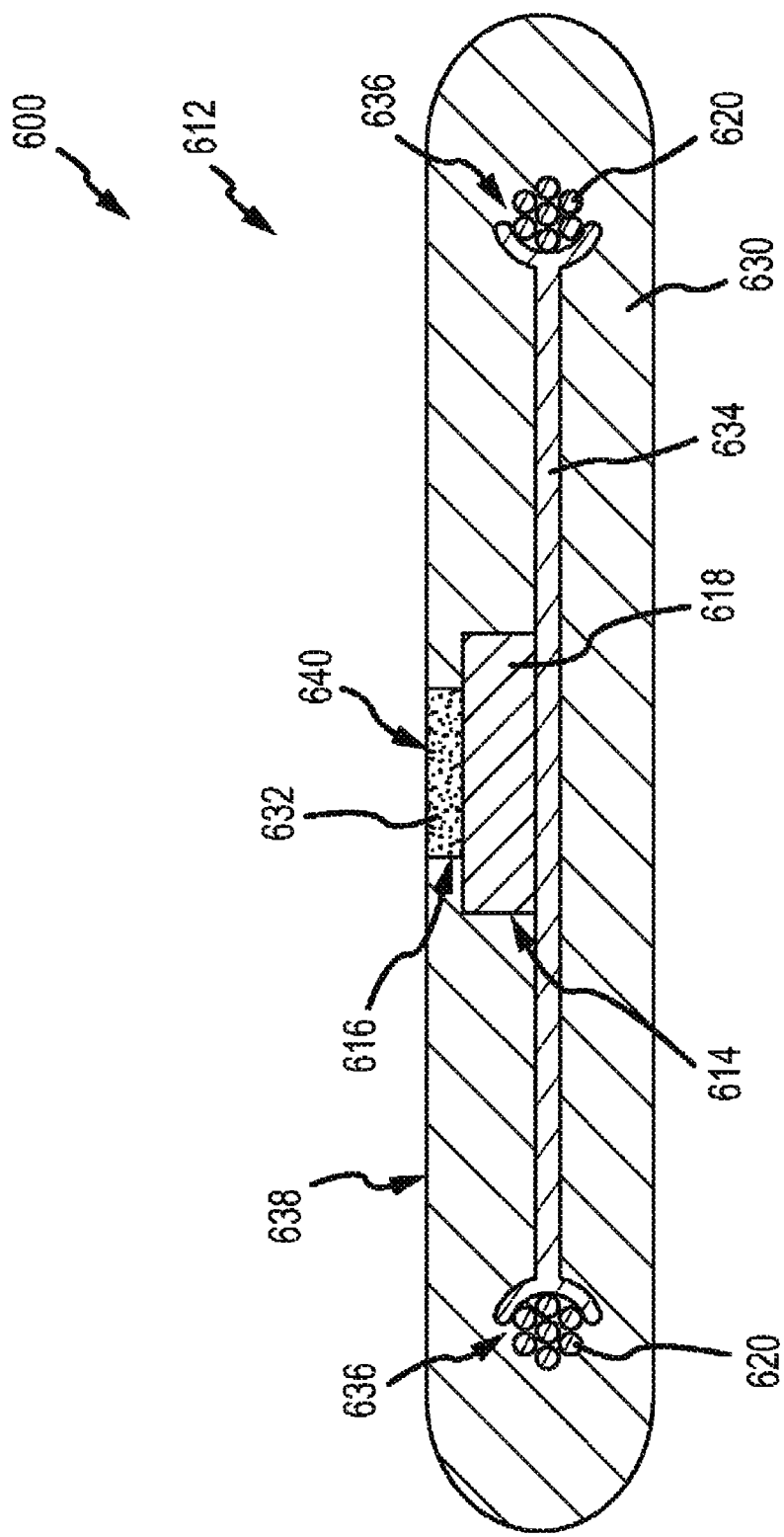
FIG. 6 is a cross-sectional view of another embodiment of an implantable portion of a cochlear implant.

FIG. 6 is a cross-sectional view of another embodiment of an implantable portion 600 of a cochlear implant. Certain components of the implantable portion 600 are described above with regard to the embodiment of FIGS. 3A and 3B, and are therefore only described briefly. The implantable portion 600 includes a biocompatible body 612 formed from a first body material 630 and a second body material 632. The first body material 630 surrounds a base 634 that provides some rigidity to the implantable portion 600, but is not required. The base 634 forms a channel or race 636 configured to at least partially receive a coil 620, formed by a winding of wires. The first body material 630 defines a pocket 614 and a throat 616 proximate an exterior surface 638 of the first body material 630. In this embodiment, the throat 616 is constricted relative to the pocket 614, such that it has a smaller area. Since the first body material 630 is flexible, the throat 616 can be deflected so as to allow insertion or removal of the magnet 618. The second body material 632 is applied so as to seal to the throat 616 to isolate the magnet 618 within the biocompatible body 612. As described elsewhere herein, the second body material 632 is applied in a liquid or viscous state. In one embodiment, after application of the second material, the upper surface 640 of the second body material 632 is shaped so as to be substantially flush with the exterior surface 638 of the first body material 630. Such shaping helps reduce the number and size of cracks, seams, or other imperfections in the biocompatible body 612, which reduces the number of sites where biofilms can form. Shaping the upper surface 640 also reduces surface variances that can cause pressure points on the skin once the implantable portion 600 is implanted in an implant site. The second body material 632 can later be at least partially separated from the body 612 so as to allow removal of the magnet 618. In certain embodiments, substantially all of the second body material 632 can be completely removed from the pocket 614 and throat 616. Methods of removing the second body material are described herein.

Figure 7:
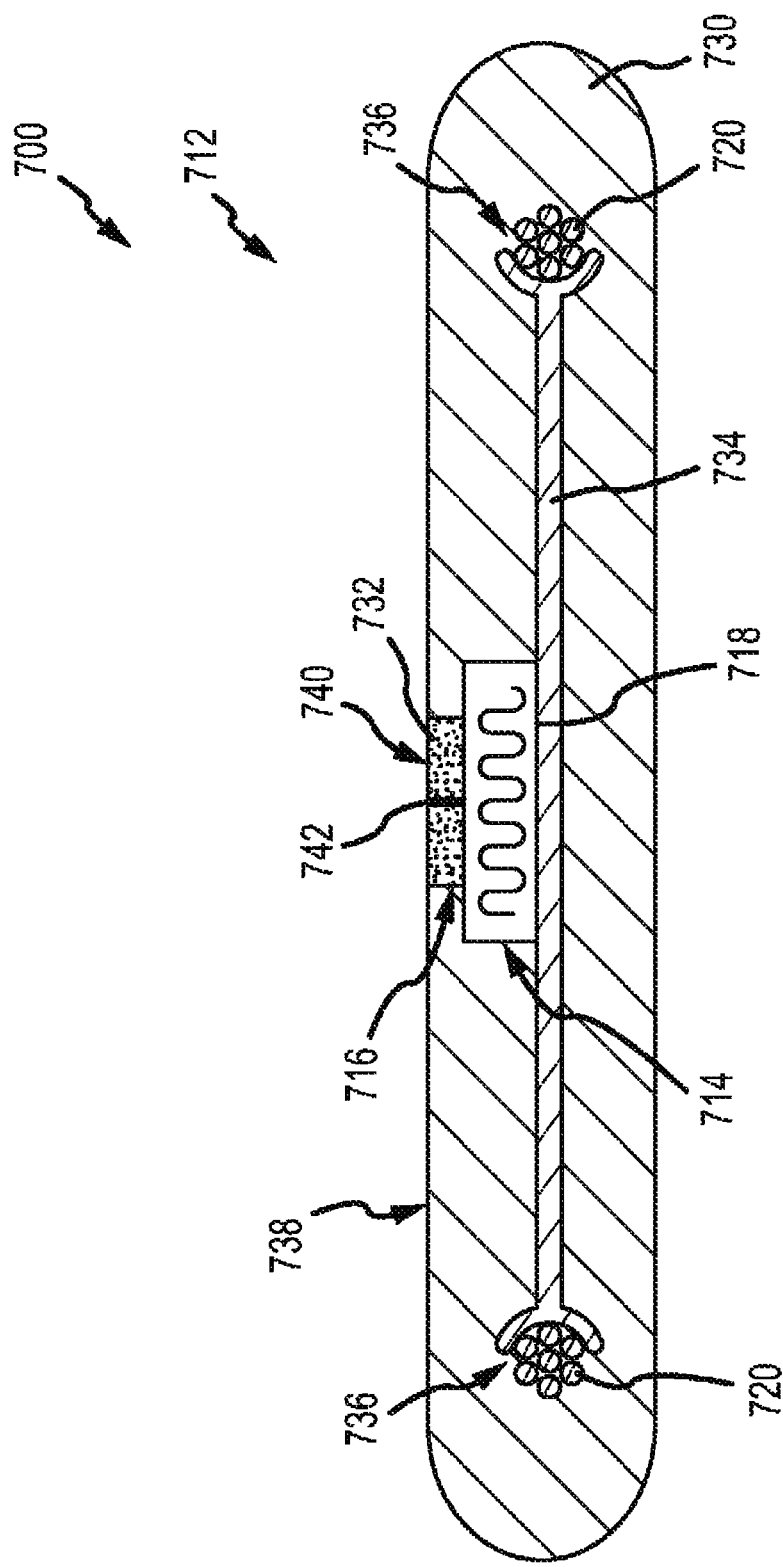
FIG. 7 is a cross-sectional view of another embodiment of an implantable portion of a cochlear implant.

FIG. 7 is a cross-sectional view of another embodiment of an implantable portion 700 of a cochlear implant. Certain components of the implantable portion 700 are described above with regard to the embodiment of FIGS. 3A and 3B, and are therefore only described briefly. The implantable portion 700 includes a biocompatible body 712 formed from a first body material 730 and a second body material 732. The first body material 730 surrounds a base 734 that provides some rigidity to the implantable portion 700, but is not required. The base 734 forms a channel or race 736 configured to at least partially receive a coil 720, formed by a winding of wires. The first body material 730 defines a pocket 714 and a throat 716 proximate an exterior surface 738 of the first body material 730. In this embodiment, the magnet 718 is a ferromagnetic fluid or a fluid containing magnetic particles. The second body material 732 forms a septum 712 through which the ferromagnetic fluid 718 can be injected to and withdrawn from the pocket 714. Thus, once implanted in a recipient, the ferromagnetic fluid 718 can be substantially withdrawn with a syringe prior to an MRI procedure. After the procedure, ferromagnetic fluid 718 can again by introduced to the pocket 714, via the septum 742. The ferromagnetic fluid 718 remains isolated from the implantation site, thus reducing the likelihood of bacterial adhesion. Although the septum 742 is formed in the second body material 732, in other embodiments, the septum can be formed in the first body material 730.

Figure 8:
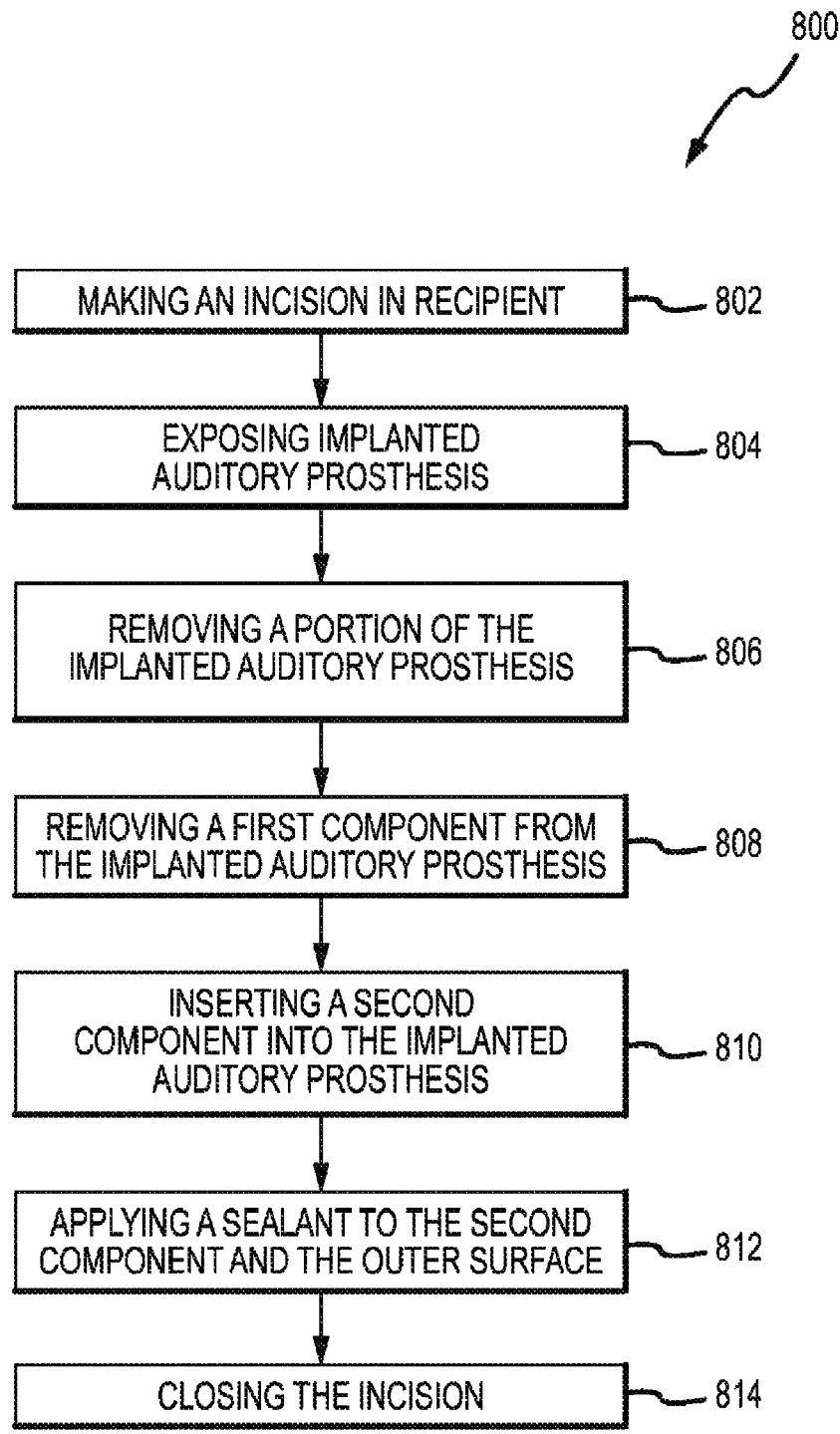
FIG. 8 depicts a method of replacing, in vivo, a component in an implanted medical device.

FIG. 8 depicts a method 800 of replacing, in vivo, a component in an implanted medical device. The method 800 is described in the context of removing a magnet from an auditory prosthesis such as a cochlear implant. The method 800 can also be used to remove any type of component from a medical device, without having to remove the entire medical device from the body. Such components that can be removed in vivo can include, e.g., batteries, coils, chips, and so on. The method 800 begins by making an incision in the implant recipient, operation 802. The skin can be withdrawn such that the incision exposes at least a portion of the cochlear implant, operation 804, typically only a portion necessary to access the magnet. A portion of the body of the cochlear implant is at least partially separated from the remainder of the body in operation 806. More specifically, as described above, a second body material is at least partially separated from a first body material. Separation can be performed by applying a tool to the second body material to physically cut the second body material from the first body material. The tool can be a manual or automatic cutting tool. Scalpels or other cutting tools common in surgical suites can be utilized. In another embodiment, a removing agent can be applied to the second body material, for example, to chemically weaken or dissolve the second body material. Weakened or dissolved material is separated from the first body material to expose the magnet. Such weakened or dissolved materials can be suctioned from the implantation site or can be removed with a tool or, when suitably biocompatible, can be reabsorbed into the patient. Second body materials can be selected that are susceptible to certain removing agents. The first body material, however, would not be susceptible to the selected removing agents. In yet another embodiment, the first body material can be deformed (e.g., stretched) to separate the second body material therefrom.

Once the portion of the body is separated, a first component (e.g., the magnet, in this example) is removed from the cochlear implant in operation 808. Although not depicted in the figure, at this time, the incision can be closed, bandaged, or otherwise protected, and a procedure performed (e.g., an MRI). Once the procedure is complete, the incision can be reopened, if required, and the method 800 continues. A second component is then inserted into the cochlear implant in operation 810. The second component can be the same magnet that was removed. In many procedures, however, the second component can be an identical, sterile component used to replace a damaged, non-sterile, or inoperable first component. For example, a dead battery can be replaced with a new battery. Thereafter, the opening into which the second component was inserted can be sealed to again isolate that component from the implant site in operation 812. This can include applying a sealant to the throat and, optionally, the magnet. The sealant can be, for example, the second body material, as described above. In other embodiments, the sealant can be a biocompatible adhesive or a non-adhesive coating. The magnet need not be completely covered by the sealant, but it is generally desirable to at least seal portions of the magnet most likely to develop biofilm adhesion. However, in certain embodiments, the magnet can be completed sealed and the top surface of the sealant can be shaped and/or finished to reduce potential sites of bacterial adhesion. Operation 812 is optional; a recipient can elect to not reseal the magnet. In such a case, the magnet remains exposed to the implantation site. The incision is then closed at the conclusion of the method 800, in operation 814.

The method 800 of FIG. 8 describes in vivo replacement of components of an implanted auditory prosthesis where separation of a second body material from the implant is required. For the implanted portion depicted in FIG. 7, the above method is altered. For example, to remove the magnetic material from the implant, a needle can be inserted to the septum and the ferromagnetic fluid withdrawn. After an MRI or other procedure, ferromagnetic fluid can be reintroduced to the pocket. Both the withdrawal and introduction operations can be performed either after an incision is made in the recipient or without making the incision (e.g., by inserting the needle through the skin and septum).

Figure 9:
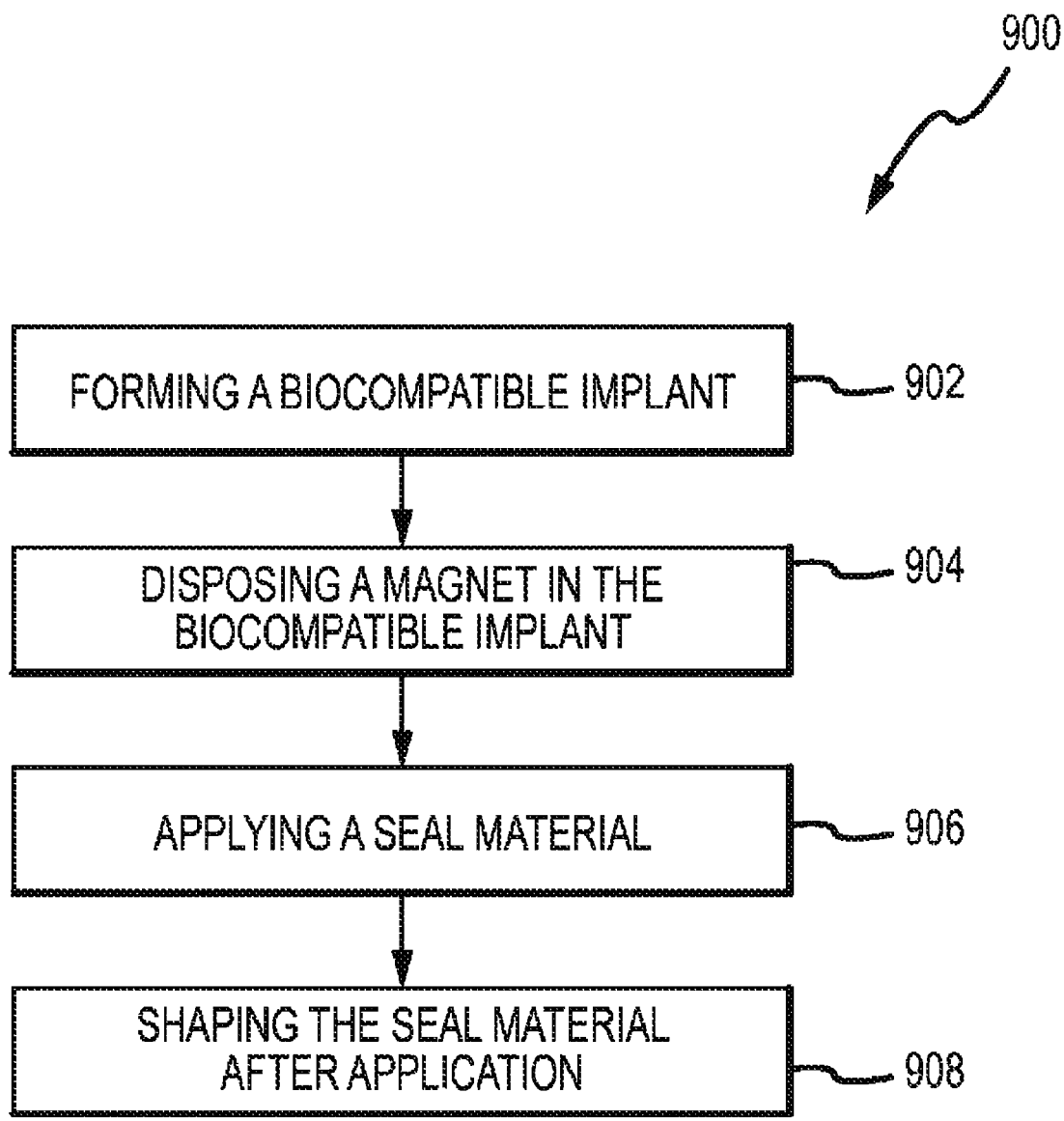
FIG. 9 depicts a method of manufacturing an implanted medical device.

FIG. 9 depicts a method 900 of manufacturing an implanted medical device, such as a cochlear implant. The method begins by forming a biocompatible implant in operation 902, such as the implantable portion of a cochlear implant, as described above. In general, forming the implant includes forming a first body material into a desired shape about a base and coil, for example, by known injection molding processes. A pocket can be formed during or after the injection molding process. A magnet is then disposed within the pocket in operation 904. A second body material is then applied to the first body material and/or magnet, operation 906, so as to isolate the magnet from a future implantation site. Application of the second body material can be when the second body material is in a liquid or viscous state. The second body material can be applied in another injection mold process or by spreading the second body material manually. In another embodiment, such as the embodiment depicted in FIGS. 5A and 5B, the second body material can be injected into a plug disposed on the magnet. Thereafter, an upper surface of the second body material can be shaped to a desired finish, operation 908.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An apparatus comprising:
   a magnet; and
   a biocompatible implant comprising a body, wherein the magnet is removably encased by the body, wherein the body comprises:
      a first body material defining a pocket and a throat in communication with the pocket, wherein the magnet is received within the pocket; and
      a second polymer body material disposed within the throat so as to isolate the magnet from exposure to an implantation site when the biocompatible implant is implanted in a recipient,
   wherein the second body material is susceptible to a chemical removing agent, and
   wherein the first body material is not susceptible to the chemical removing agent.

2. The apparatus of claim 1, wherein the second body material forms a seal with the first body material.

3. The apparatus of claim 1, wherein the second body material is at least partially separable from the body.

4. The apparatus of claim 1, wherein the throat is constricted relative to the pocket.

5. The apparatus of claim 1, further comprising a plug secured to the magnet, wherein the plug defines a plug cross-sectional area less than a throat cross-sectional area.

6. The apparatus of claim 5, and wherein the second body material is disposed between the plug and the throat when the magnet is received in the first body material.

7. A method comprising:
   making an incision in a recipient of a biocompatible implant so as to expose at least a portion of the biocompatible implant, wherein the biocompatible implant comprises a body and a first component removably encased in the body;
   exposing the first component by removing at least a portion of the body that removably encases the first component, wherein the removed portion of the body comprises a polymer material different than a remainder of the body; and
   removing the first component from the body, while the biocompatible implant is implanted within the recipient,
   wherein exposes the first component comprises applying a chemical removing agent to which a second body material is susceptible and to which a first body material is not susceptible.

8. The method of claim 7, wherein the body comprises the first body material and the second body material comprising the polymer material.

9. The method of claim 8, wherein exposing the first component comprises at least partially separating the second body material from the body.

10. The method of claim 9, wherein separating the second body material from the body comprises applying a tool to the second body material.

11. The method of claim 7, further comprising:
    inserting a second component into the body; and
    closing the incision.

12. The method of claim 11, further comprising applying a sealant to the second component and the body, so as to isolate the second component from microbial contact within an implant site of the recipient.

13. The method of claim 11, wherein the second component is substantially the same as the first component.

14. The method of claim 12, wherein the sealant is different than the second body material.

15. A method comprising:
    forming a biocompatible implant comprising a body comprising a first body material that is not susceptible to a chemical removing agent;
    disposing a magnet within the first body material; and
    thereafter, applying a second body material that is susceptible to the chemical removing agent to the first body material so as to isolate the magnet from microbial contact, wherein the second body material is a polymer.

16. The method of claim 15, further comprising shaping the second body material after application.

* * * * *